United States Patent
Thosar et al.

(10) Patent No.: US 9,750,481 B2
(45) Date of Patent: Sep. 5, 2017

(54) SYSTEM AND METHOD FOR ANALYZING ANTEGRADE AND RETROGRADE BLOOD FLOW

(71) Applicant: Indiana University Research and Technology Corporation, Indianapolis, IN (US)

(72) Inventors: Saurabh S. Thosar, Beaverton, OR (US); Janet P. Wallace, Bloomington, IN (US); Chad C. Wiggins, Bloomington, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 153 days.

(21) Appl. No.: 14/751,458

(22) Filed: Jun. 26, 2015

(65) Prior Publication Data

US 2015/0379736 A1 Dec. 31, 2015

Related U.S. Application Data

(60) Provisional application No. 62/017,569, filed on Jun. 26, 2014.

(51) Int. Cl.
*G06K 9/00* (2006.01)
*A61B 8/08* (2006.01)
*A61B 8/06* (2006.01)

(52) U.S. Cl.
CPC .............. *A61B 8/5223* (2013.01); *A61B 8/06* (2013.01); *A61B 8/0891* (2013.01); *G06T 2207/30104* (2013.01)

(58) Field of Classification Search
None
See application file for complete search history.

(56) References Cited

U.S. PATENT DOCUMENTS

2012/0136242 A1* 5/2012 Qi .................. A61B 5/026
600/424
2015/0379736 A1* 12/2015 Thosar ................ A61B 8/06
382/131

OTHER PUBLICATIONS

Steffens et al., Quantification of collateral blood flow in coarctation of the aorta by velocity encoded cine magnetic resonance imaging. Circulation. 1994;90:937-943, Originally published Aug. 1, 1994. Available online: https://doi.org/10.1161/01.CIR.90.2.937. Or also available online at http://circ.ahajournals.org/content/90/2/937. short.*

* cited by examiner

*Primary Examiner* — Tahmina Ansari
(74) *Attorney, Agent, or Firm* — Stinson Leonard Street LLP (57) ABSTRACT

A computer-implemented method for simultaneously analyzing antegrade and retrograde blood flow is provided. The method is implemented using a computing device including a processor in communication with a memory. The method includes receiving a first plot of blood velocities over time and determining a first amount of blood flow based on the first plot. The first amount is associated with antegrade blood flow. The method additionally includes determining a second amount of blood flow based on the first plot. The second amount is associated with retrograde blood flow. Additionally, the method includes determining a mean amount of blood flow based at least in part on the first amount of blood flow and the second amount of blood flow, and storing at least one of the first amount, the second amount, and the mean amount of blood flow in the memory.

20 Claims, 9 Drawing Sheets

SYSTEM AND METHOD FOR ANALYZING ANTEGRADE AND RETROGRADE BLOOD FLOW

CROSS REFERENCE TO RELATED APPLICATION

This application claims priority to U.S. Provisional Patent Application No. 62/017,569 filed on Jun. 26, 2014, which is incorporated by reference herein in its entirety.

BACKGROUND

This description relates to analyzing blood flow within a blood vessel, and more specifically to analyzing antegrade blood flow and retrograde blood flow within the blood vessel.

At least some known ultrasound computing devices generate Doppler information that represents the velocity of blood through a vessel over time. The information is, in some systems, represented as a plot of velocity (i.e., on a y-axis) versus time (i.e., on an x-axis). Some known systems utilize velocity data associated with flow in an antegrade (i.e., forward) direction, to determine an amount of blood flow in the antegrade direction for a given period of time. However, no known systems utilize velocity information associated with the flow in the retrograde (i.e., reverse) direction for a given period of time to concurrently determine an amount of blood flow in the retrograde direction. Accordingly, determining the amount of blood flow in the retrograde direction for a given period of time may be difficult and time-consuming for a user of such systems.

BRIEF DESCRIPTION OF THE DISCLOSURE

In one aspect, a computer-implemented method for simultaneously analyzing antegrade and retrograde blood flow is provided. The method is implemented using a computing device including a processor in communication with a memory. The method includes receiving, by the computing device, a first plot of blood velocities over time and determining, by the computing device, a first amount of blood flow based on the first plot. The first amount is associated with antegrade blood flow. The method additionally includes determining, by the computing device, a second amount of blood flow based on the first plot. The second amount is associated with retrograde blood flow. Additionally, the method includes determining, by the computing device, a mean amount of blood flow based at least in part on the first amount of blood flow and the second amount of blood flow, and storing at least one of the first amount of blood flow, the second amount of blood flow, and the mean amount of blood flow in the memory.

In another aspect, a computing device for simultaneously analyzing antegrade and retrograde blood flow is provided. The computing device includes a processor in communication with a memory device. The computing device is configured to receive a first plot of blood velocities over time and determine a first amount of blood flow based on the first plot. The first amount is associated with antegrade blood flow. The computing device is additionally configured to determine a second amount of blood flow based on the first plot. The second amount is associated with retrograde blood flow. Additionally, the computing device is configured to determine a mean amount of blood flow based at least in part on the first amount of blood flow and the second amount of blood flow, and store at least one of the first amount of blood flow, the second amount of blood flow, and the mean amount of blood flow in the memory device.

In yet another aspect, a computer-readable storage medium having computer-executable instructions embodied thereon is provided. When executed by a computing device having a processor in communication with a memory device, the computer-executable instructions cause the computing device to receive a first plot of blood velocities over time and determine a first amount of blood flow based on the first plot. The first amount is associated with antegrade blood flow. Additionally, the instructions cause the computing device to determine a second amount of blood flow based on the first plot. The second amount is associated with retrograde blood flow. Additionally, the instructions cause the computing device to determine a mean amount of blood flow based at least in part on the first amount of blood flow and the second amount of blood flow, and store at least one of the first amount of blood flow, the second amount of blood flow, and the mean amount of blood flow in the memory device.

BRIEF DESCRIPTION OF THE DRAWINGS

FIGS. 1-9 show example embodiments of the methods and systems described herein.

DETAILED DESCRIPTION OF THE DISCLOSURE

Implementations of systems described herein analyze antegrade and retrograde blood flow based on data generated by an ultrasound computing device. More specifically, implementations of the systems described herein receive one or more plots of the blood velocities within a blood vessel and determine the amount of antegrade blood flow, the amount of retrograde blood flow, and the mean amount of blood flow through the vessel for a given period of time. In some implementations, the system receives image data, for example an image of the plot. In other implementations, the system receives a video including a plurality of images, each including a plot. In such implementations, the system identifies the plot within each image and determines the blood flow amounts based on the plot. More specifically, in some implementations, each plot represents the velocities of the blood over time, for example in centimeters per second, through the vessel. The plot indicates a positive velocity as the blood moves in an antegrade direction through the vessel, and indicates a negative velocity as the blood moves in a retrograde direction through the vessel. Accordingly, the system determines metrics based on the velocities including, for example, an amount of antegrade blood flow, an amount of retrograde blood flow, and a mean amount of blood flow. In some implementations, the system stores one or more of the metrics in a memory, such as in a database or a spreadsheet.

The methods and systems described herein may be implemented using computer programming or engineering techniques including computer software, firmware, hardware or any combination or subset thereof, wherein the technical effect may include at least one of: (a) receiving a first plot of blood velocities over time; (b) determining a first amount of blood flow based on the first plot, the first amount is associated with antegrade blood flow; (c) determining a second amount of blood flow based on the first plot, the second amount is associated with retrograde blood flow; (d) determining a mean amount of blood flow based at least in part on the first amount of blood flow and the second amount of blood flow; and (e) storing at least one of the first amount of blood flow, the second amount of blood flow, and the mean amount of blood flow in a memory.

In one embodiment, a computer program is provided, and the program is embodied on a computer-readable medium. In an example embodiment, the system is executed on a single computer system, without requiring a connection to a server computer. In a further example embodiment, the system is being run in a WINDOWS® environment (Windows is a registered trademark of Microsoft Corporation, Redmond, Wash.). In yet another embodiment, the system may be run on a mainframe environment and a UNIX® server environment (UNIX is a registered trademark of AT&T located in New York, N.Y.). The application is flexible and designed to run in various different environments without compromising any major functionality. In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes.

The following detailed description illustrates embodiments of the disclosure by way of example and not by way of limitation. It is contemplated that the disclosure has general application to analyzing blood flow information in healthcare and research applications.

As used herein, an element or step recited in the singular and preceded with the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

Figure 1:
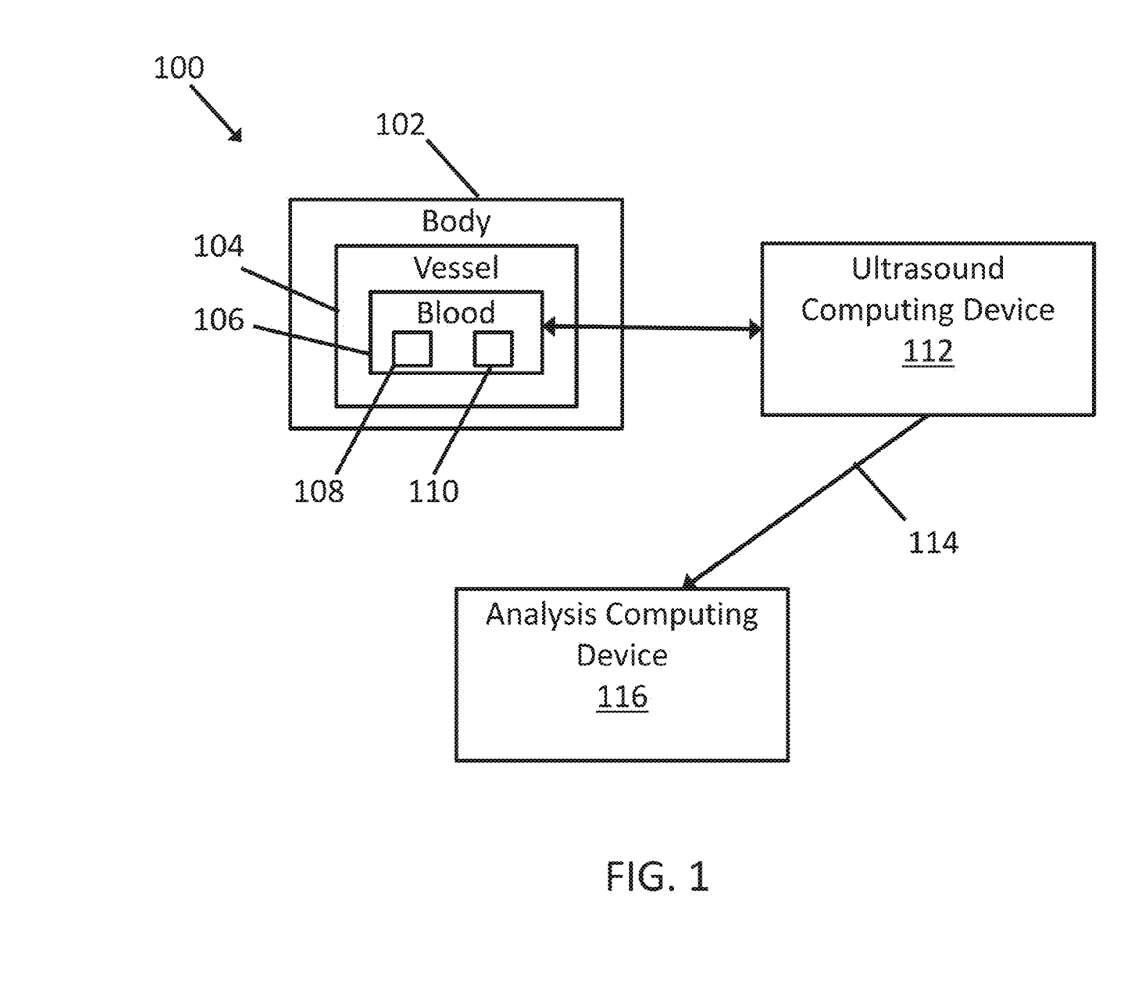
FIG. 1 is a schematic diagram illustrating an example environment in which an ultrasound computing device generates data regarding blood velocities within a body for analysis by an analyzer computing device.
Figure 3:
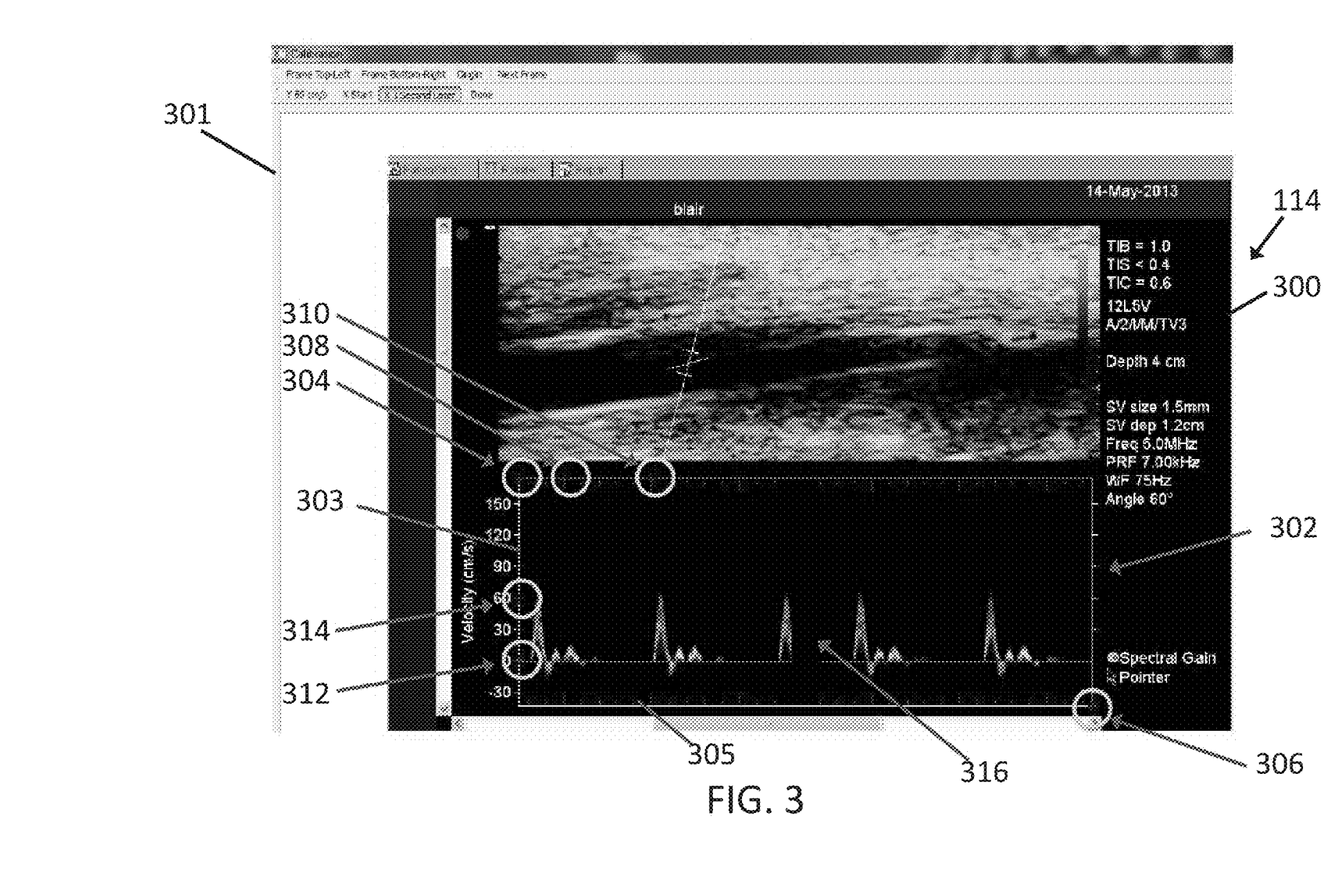
FIG. 3 is an example image generated by the ultrasound computing device included within FIG. 1.

FIG. 1 is a schematic diagram illustrating an example environment 100 including a body 102, an ultrasound computing device 112, and an analyzer computing device 116. Body 102 includes a vessel 104 through which blood 106 flows. The flow of blood 106 includes an antegrade flow component 108 and a retrograde flow component 110. More specifically, on a cyclic basis, for example with each beat of a heart (not shown) in body 102, blood 106 flows alternately in an antegrade direction and in a retrograde direction. Ultrasound computing device 112 monitors the flow of blood 106 using, for example, Doppler imaging, and generates data 114 regarding the velocity blood 106 over time. For example, in some implementations, ultrasound computing device 112 generates images that each include a plot 302 (FIG. 3) of the velocity of blood 106 over time (FIG. 3). Analyzer computing device 116 receives data 114 and determines, an amount of antegrade blood flow, an amount of retrograde blood flow, and a mean amount of blood flow for a given time period. For example, in some implementations, analyzer computing device 116 analyzes plot 302 or a portion of plot 302 corresponding to a predefined period of time, and determines the blood flow amounts for the predefined period of time. In some implementations, analyzer computing device 116 additional identifies a maximum blood velocity during the predefined period of time and/or an average blood velocity during the predefined period of time.

Figure 2:
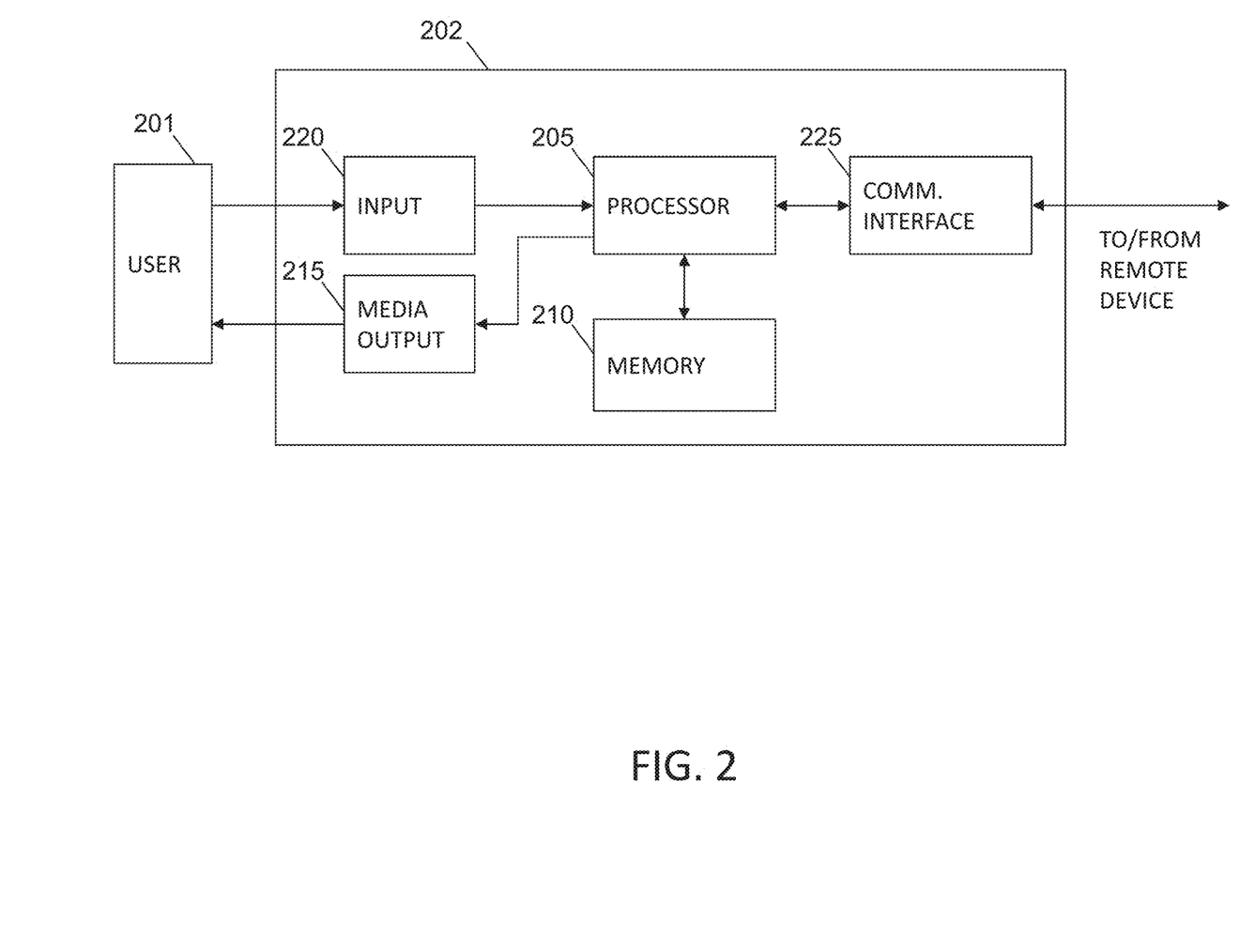
FIG. 2 is an example configuration of a computing device used within the environment shown in FIG. 1.

FIG. 2 illustrates an example configuration of a computing device 202 used within environment 100. Computing device 202 is representative of ultrasound computing device 112 and analyzer computing device 116. More specifically, implementations of ultrasound computing device 112 and analyzer computing device 116 may include all or a subset of components of computing device 202 and/or additional components. For example, ultrasound computing device 112 additionally includes a transceiver (not shown) that transmits and receives ultrasonic waves.

Computing device 202 includes one or more processors 205 for executing instructions. In some embodiments, executable instructions are stored in one or more memory devices 210. Processor 205 may include one or more processing units (e.g., in a multi-core configuration). One or more memory devices 210 are any one or more devices allowing information such as executable instructions and/or other data to be stored and retrieved. One or more memory devices 210 may include one or more computer-readable media and/or one or more databases. One or more memory devices 210 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), non-volatile RAM (NVRAM), and/or one or more hard disks or solid state disks. The above memory types are example only, and are thus not limiting as to the types of memory usable for storage of a computer program and/or data.

Computing device 202 also includes at least one media output component 215 for presenting information to user 201. Media output component 215 is any component capable of conveying information to user 201. In some embodiments, media output component 215 includes an output adapter such as a video adapter and/or an audio adapter. An output adapter is operatively coupled to processor 205 and operatively couplable to an output device such as a display device (e.g., a liquid crystal display (LCD), organic light emitting diode (OLED) display, cathode ray tube (CRT), or "electronic ink" display) or an audio output device (e.g., a speaker or headphones).

In some embodiments, computing device 202 includes an input device 220 for receiving input from user 201. Input device 220 may include, for example, a keyboard, a pointing device, a mouse, a stylus, a touch sensitive panel (e.g., a touch pad or a touch screen), or an audio input device. A single component such as a touch screen may function as both an output device of media output component 215 and input device 220.

Computing device 202 may also include a communication interface 225, which is communicatively couplable to a remote device such as another computing device. Communication interface 225 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in one or more memory devices 210 are, for example, computer-readable instructions for providing a user interface to user 201 via media output component 215 and, optionally, receiving and processing input from input device 220.

FIG. 3 is an example image 300 generated by ultrasound computing device 112. More specifically, image 300 is an example of data 114 that is generated by ultrasound computing device 112 and received by analyzer computing device 116. Analyzer computing device 116 displays image 300 in a user interface 301. Image 300 includes a plot 302 of blood velocities over time. In some implementations, plot 302 represents the velocity of blood 106 in centimeters per second on a y-axis 303, and represents time in seconds on an x-axis 305. A plurality of reference points including a first reference point 304, a second reference point 306, a third reference point 308, a fourth reference point 310, a fifth reference point 312, and a sixth reference point 314 correspond to respective portions of plot 302. More specifically, first reference point 304 corresponds to an upper-left corner of plot 302. Second reference point 306 corresponds to a lower-right corner of plot 302. Analyzer computing device 116 may utilize first reference point 304 and second reference point 306 to identify the location and boundaries of plot 302 within image 300.

Third reference point 308 and fourth reference point 310 correspond to a beginning and an end of a first time period for which analyzer computing device determines a set of metrics including an antegrade blood flow amount, a retrograde blood flow amount, a mean blood flow amount, a maximum velocity, and an average velocity of the blood. In some implementations, analyzer computing device 116 generates a mathematical function to fit the velocities represented in plot 302, using, for example, a curve fitting process. In some implementations, analyzer computing device 116 determines the antegrade blood flow amount by integrating the mathematical function for portions of the first time period associated with positive velocities of the blood. In some implementations, analyzer computing device 116 determines the retrograde blood flow amount by integrating the mathematical function for portions of the first time period associated with negative velocities of the blood. In other implementations, rather than generating a mathematical function and integrating the function, analyzer computing device 116 identifies the velocity at each of a plurality of times along the x-axis over the first time period. In such implementations, analyzer computing device 116 sums the positive velocities to determine the antegrade flow amount and sums the negative velocities to determine the retrograde flow amount.

Analyzer computing device 116 determines the mean blood flow amount by subtracting the retrograde blood flow amount from the antegrade blood flow amount. Analyzer computing device 116 identifies the maximum velocity during the first time period, for example, by identifying a velocity value greater than any other values in the first time period. Analyzer computing device 116 determines the average velocity, for example, by dividing the mean blood flow amount by the first time period. Fourth reference point 310 represents an ending of the first period. Analyzer computing device 116 additionally analyzes subsequent time periods. For example, analyzer computing device 116 determines a second set of metrics including an antegrade blood flow amount, a retrograde blood flow amount, a mean blood flow amount, a maximum velocity, and an average velocity of the blood for a second time period occurring after the first time period (i.e., after fourth reference point 310). Fifth reference point 312 corresponds to an origin in plot 302. Sixth reference point 314 is a calibration point representing a fixed or predefined velocity, for example 60 cm/s.

In some implementations, analyzer computing device 116 receives input, for example through input device 220, designating one or more of first reference point 304, second reference point 306, third reference point 308, fourth reference point 310, fifth reference point 312, and sixth reference point 314. In some implementations, analyzer computing device 116 identifies one or all of first reference point 304, second reference point 306, third reference point 308, fourth reference point 310, fifth reference point 312, and sixth reference point 314 without receiving designations of the points through input device 220. In some implementations, analyzer computing device 116 identifies a location of the most recent blood velocity information generated by ultrasound computing device 112 based, at least in part, on a location of a marker 316. More specifically, marker 316 is a break in the velocity information at the particular instant in time corresponding to image 300. In subsequent images, velocity data appears at the location of marker 316 in image 300, and in such subsequent images, marker 316 is at a location further along x-axis 305. More specifically, in image 300, blood velocity information immediately to the left of marker 316 is the most recent blood velocity information generated by ultrasound computing device for the instant in time represented by image 300.

In some implementations, image 300 is one image or frame in a plurality of images included in data 114. For example, data 114 may include a video, wherein each frame of the video is a separate image 300. In such implementations, the video has an associated number of frames per second (e.g., five frames per second). Analyzer computing device 116 may determine the frames per second through analysis of a meta information encoded in a file containing the video, may receive a designation of the frames per second from user 201 through input device 220, and/or may determine the frames per second from other techniques, such as image analysis. In some implementations, analyzer computing device 116 determines an antegrade blood flow amount, a retrograde blood flow amount, a mean blood flow amount, a maximum velocity, and an average velocity of the blood for a fixed time period associated with each image 300 or plot 302, based for example on the frames per second. For example, if the video includes five frames per second, then analyzer computing device 116 determines metrics including an antegrade blood flow amount, a retrograde blood flow amount, a mean blood flow amount, a maximum velocity, and an average velocity of the blood for every 0.2 seconds (i.e., $\frac{1}{5}^{th}$ of a second) that elapse. In some implementations, analyzer computing device 116 determines such metrics for the entire length of the video, or for another specified time period. Analyzer computing device 116 may store the metrics in memory device 210. In some implementations, analyzer computing device 116 stores the metrics in one or more tables of a database. In other implementations, analyzer computing device 116 stores the metrics in a spreadsheet or in another format, such as comma-separated values.

Figure 4:
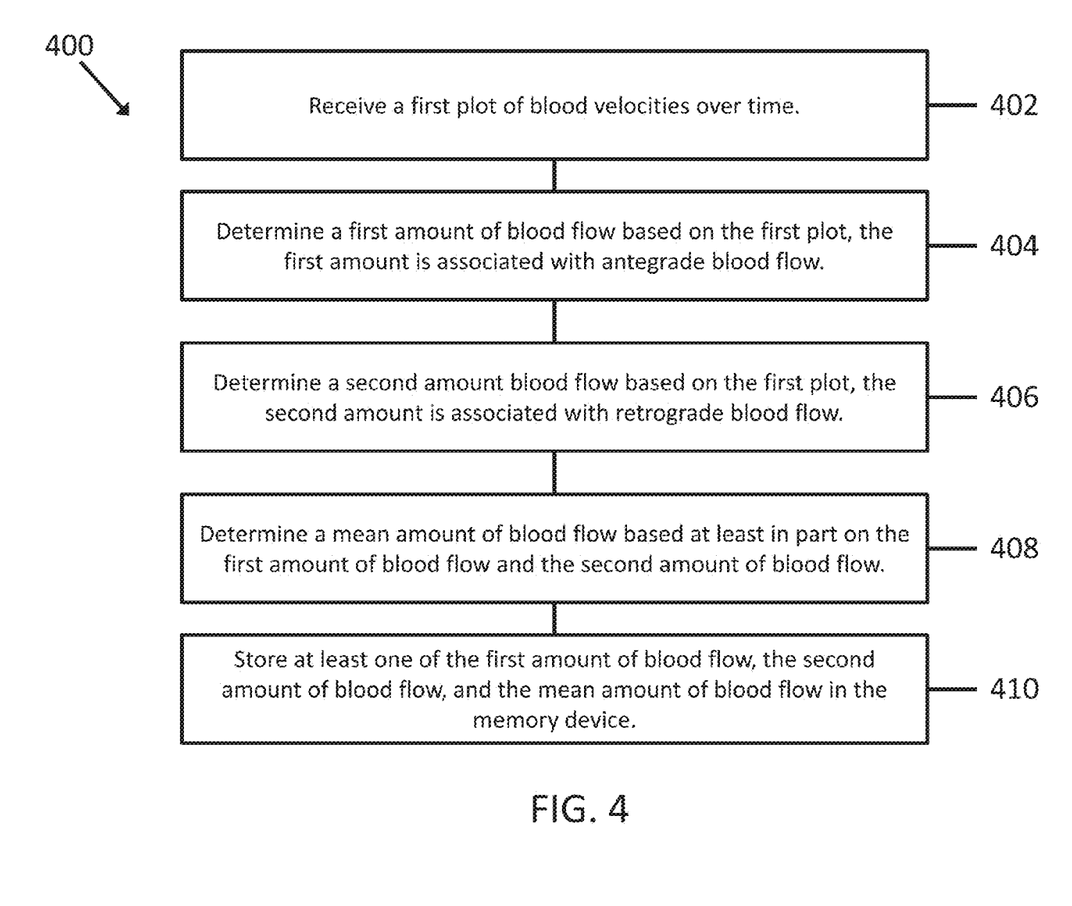
FIG. 4 is a flowchart of an example process that may be performed by the analyzer computing device for analyzing antegrade and retrograde blood flow.

FIG. 4 is a flowchart of an example process that may be performed by analyzer computing device 116 for analyzing antegrade and retrograde blood flow. Initially, analyzer computing device 116 receives 402 a first plot 302 of blood velocities over time. Additionally, analyzer computing device 116 determines 404 a first amount of blood flow based on the first plot 302. The first amount is associated with antegrade blood flow. Additionally, analyzer computing device 116 determines 406 a second amount of blood flow based on the first plot 302. The second amount of blood flow is associated with retrograde blood flow. In some implementations, analyzer computing device 116 determines the first amount and the second amount simultaneously. For example, in some implementations, analyzer computing device 116 determines both the first amount and the second amount without requiring manipulation (e.g., inversion) of first plot 302 between determining the first amount and determining the second amount. Additionally, analyzer computing device 116 determines 408 a mean amount of blood flow based at least in part on the first amount of blood flow and the second amount of blood flow. For example, analyzer computing device 116 subtracts the second amount of blood flow (i.e., retrograde blood flow) from the first amount of blood flow (i.e., antegrade blood flow) to arrive at the mean amount of blood flow. Additionally, analyzer computing device 116 stores 410 at least one of the first amount of blood flow, the second amount of blood flow, and the mean amount of blood flow in memory device 210 for example, in one or more tables of a database, in a spreadsheet or in another format, such as in a file of comma-separated values.

In some implementations, analyzer computing device 116 receives a plurality of plots, including first plot 302, wherein each plot corresponds to a fixed time period, such as the first time period and the second time period, described above. Additionally, in some implementations, analyzer computing device 116 determines the first amount of blood flow, the second amount of blood flow, and the mean amount of blood flow for each fixed time period. In some implementations, analyzer computing device 116 identifies a portion of first plot 302 that corresponds to a most recent output of ultrasound computing device 112 over the fixed time period (i.e., the first time period) and determines the first amount of blood flow, the second amount of blood flow, and the mean amount of blood flow based on the identified portion. In some implementations, analyzer computing device 116 receives a first image 300 generated by ultrasound computing device 112 and identifies first plot 302 in first image 300. In some implementations, analyzer computing device 116 receives an input designating at least one reference point on first image 300 and identifies first plot 302 based at least in part on the at least one reference point. In some implementations, analyzer computing device 116 receives a video that includes a plurality of images generated by ultrasound computing device 112, identifies first plot 302 in first image 300 of the plurality of images, and identifies at least a second plot in a second image of the plurality of images. In some implementations, analyzer computing device 116 determines a number of frames per second from the plurality of images and sets the fixed time period based on the frames per second. In some implementations, analyzer computing device 116 identifies a maximum blood velocity, based at least in part on first plot 302. More specifically, in some implementations, analyzer computing device 116 determines at least one of a maximum antegrade blood velocity and a maximum retrograde blood velocity. In some implementations, analyzer computing device 116 determines an average blood velocity based at least in part on first plot 302. In some implementations, analyzer computing device 116 determines at least one of an average antegrade blood velocity and an average retrograde blood velocity.

Figure 5:
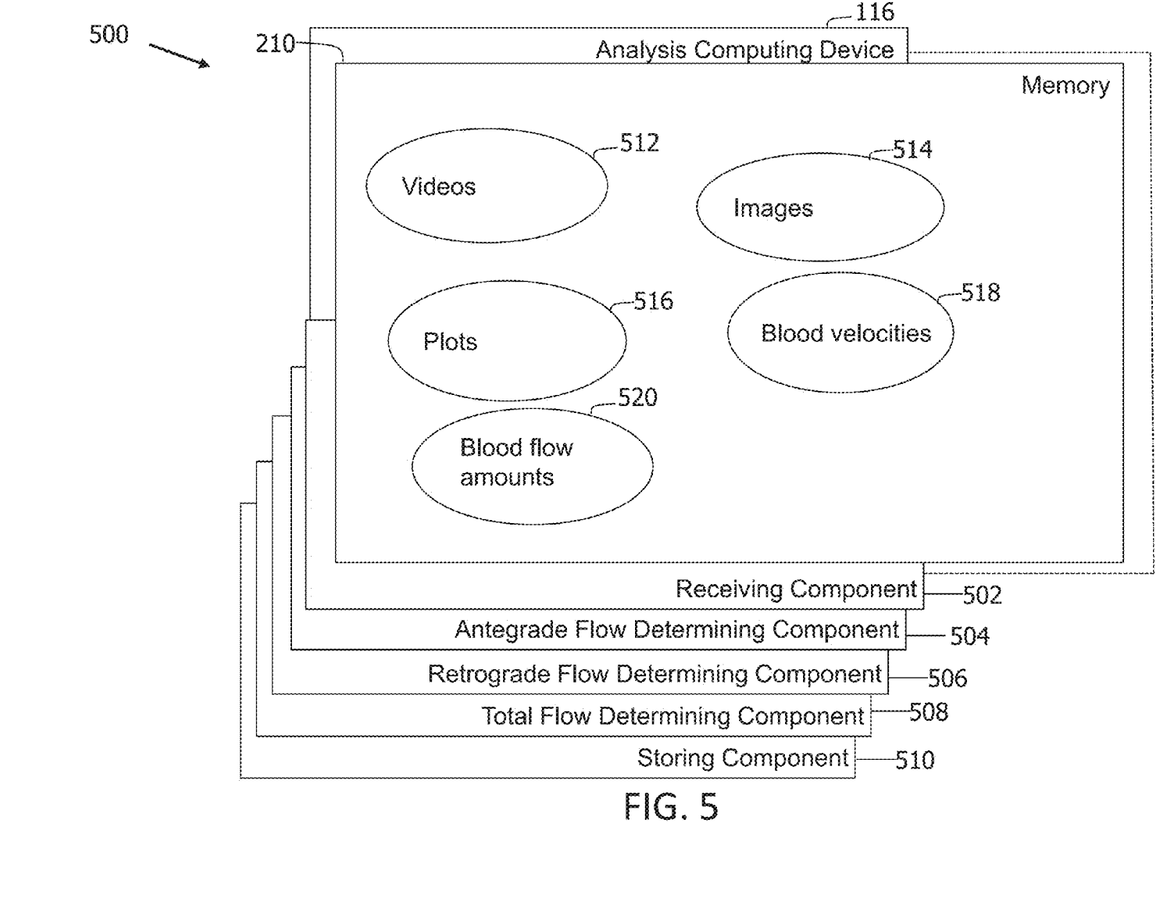
FIG. 5 is a diagram of components of one or more example computing devices that may be used in embodiments of the described systems and methods.

FIG. 5 is a diagram 500 of components of one or more example computing devices, for example, analyzer computing device 116 that may be used in implementations of the described systems and methods. FIG. 5 further shows a configuration of data stored in memory device 210 (FIG. 2).

Analyzer computing device 116 includes a receiving component 502 for receiving a first plot 302 of blood velocities over time. Analyzer computing device 116 additionally includes an antegrade flow determining component 504 for determining a first amount of blood flow based on first plot 302. The first amount is associated with antegrade blood flow. Analyzer computing device 116 additionally includes a retrograde flow determining component 506 for determining a second amount blood flow based on first plot 302. The second amount is associated with retrograde blood flow. Additionally, analyzer computing device 116 includes a mean flow determining component 508 for determining a mean amount of blood flow based at least in part on the first amount of blood flow and the second amount of blood flow. Additionally, analyzer computing device 116 includes a storing component 510 for storing at least one of the first amount of blood flow, the second amount of blood flow, and the mean amount of blood flow in memory device 210. For example, the data may be stored in one or more tables of a database, in a spreadsheet, in comma-separated values, or in another format.

In an example embodiment, data stored in memory device 210 is divided into a plurality of sections, including but not limited to, a videos section 512, an images section 514, a plots section 516, a blood velocities section 518, and a blood flow amounts section 520. In at least some implementations, these sections within memory device 210 are interconnected to retrieve and store information in accordance with the functions and processes described above.

The term processor, as used herein, refers to central processing units, microprocessors, microcontrollers, reduced instruction set circuits (RISC), application specific integrated circuits (ASIC), logic circuits, and any other circuit or processor capable of executing the functions described herein.

As used herein, the terms "software" and "firmware" are interchangeable, and include any computer program stored in memory for execution by one or more processors 205, including RAM memory, ROM memory, EPROM memory, EEPROM memory, and non-volatile RAM (NVRAM) memory. The above memory types are example only, and are thus not limiting as to the types of memory usable for storage of a computer program.

As will be appreciated based on the foregoing specification, the above-discussed embodiments of the disclosure may be implemented using computer programming or engineering techniques including computer software, firmware, hardware or any combination or subset thereof. Any such resulting computer program, having computer-readable and/or computer-executable instructions, may be embodied or provided within one or more computer-readable media, thereby making a computer program product, i.e., an article of manufacture, according to the discussed embodiments of the disclosure. These computer programs (also known as programs, software, software applications or code) include machine instructions for a programmable processor, and can be implemented in a high-level procedural and/or object-oriented programming language, and/or in assembly/machine language. As used herein, the terms "machine-readable medium," "computer-readable medium," and "computer-readable media" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium," "computer-readable medium," and "computer-readable media," however, do not include transitory signals (i.e., they are "non-transitory"). The term "machine-readable signal" refers to any signal used to provide machine instructions and/or data to a programmable processor.

The above-described embodiments of a method and system for analyzing antegrade and retrograde blood flow determine an amount of blood flow in an antegrade direction, an amount of blood flow in a retrograde direction, and a mean amount of blood flow for a given period of time. Accordingly, embodiments of the systems and methods described herein provide more complete information regarding blood amounts in antegrade and retrograde directions than known systems.

The disclosure will be more fully understood upon consideration of the following non-limiting Examples.

EXAMPLES

Example 1

In this Example, the effect of prolonged sitting on endothelial function was analyzed at least in part by the system described herein. Particularly, prolonged sitting of subjects was studied to analyze its effects of superficial femoral artery (SFA) endothelial function.

Male subjects had to self-report that they were nonsmokers, and not taking any anti-hypertensive, lipid lowering, and/or anti-diabetic medications. To be included, they needed to have total cholesterol ≤240 mg/dL and triglycerides ≤200 mg/dL. Subjects were recruited who performed less than 150 minutes/week of moderate intensity physical activity or less than 75 minutes/week of vigorous intensity physical activity. Subjects were asked to maintain their regular diet patterns throughout the study duration and to discontinue any over the counter antioxidant supplement at least 7 days prior to the first session.

Two screening visits and two sitting trials in random sequence, one with uninterrupted sitting (SIT) and one with oral Vitamin C during the sitting time (VIT) were conducted. Specifically, SIT represents prolonged 3 hours of sitting. VIT represents prolonged sitting with intermittent vitamin C. Flow mediated dilation (FMD) was measured at 0, 1, 2 and 3 hours. Subjects ingested 1 g vitamin C at 30 minutes and 500 mg at 1 hour 30 minutes.

Screening Visits:

At the first visit, all experimental procedures were explained to the subjects and they were familiarized with the lab setting. Height, weight and blood pressure were measured using standard procedures and a medical health history and habits questionnaire was completed to screen for any preexisting cardiovascular or metabolic conditions and to screen for physical activity criteria. Blood pressure was measured during an additional screening visit, at the same time of day, to confirm previous measurements.

Testing Trials:

Subjects arrived at the laboratory after an overnight fast of at least 6 hours between 7:00 AM and 9:00 AM. The arrival time was matched for both trials within each subject. Subjects were also asked to refrain from any caffeinated drink for at least 8 hours before reporting to the lab. Upon their arrival in the lab, all subjects self-reported adhering to the fasting schedule. During both trials, the subjects remained seated for 3 hours without moving their legs or feet. Subjects were allowed to move their arms, not vigorously, for example to use a computer or do light reading during the non-testing periods of the trials. Arm movement was not quantified. The flow mediated dilation (FMD) and other vascular function parameters were measured at baseline, 1 hour, 2 hours and 3 hours into testing.

The two trials were performed in random order, separated by a minimum of two and a maximum of seven days. The SIT trial was uninterrupted sitting for 3 hours, whereas in the VIT trial, subjects ingested two Vitamin C tablets; 1 g at 30 minutes and 500 mg at 1 hour 30 minutes during the sitting interval.

Superficial Femoral Artery (SFA) FMD:

Endothelial function was measured using SFA FMD, measured in accordance with current guidelines. SFA was chosen for two reasons: (1) it is a readily accessible artery for measuring FMD in a sitting position; and (2) SFA FMD has been shown to be largely nitric oxide (NO) dependent. Each measurement was performed in a dark, quiet and climate controlled (22-25° C.) room. A 5×84 cm automatic blood pressure cuff (E-20 rapid cuff inflator; D. E. Hokanson, Bellevue, Wash., USA) was placed on the subject's right thigh about 7 cm above the knee joint, distal to the SFA recording location. Images of the SFA were obtained longitudinally 7-10 cm below the inguinal line with a 2-D high-resolution ultrasound system (Terason t3000, Teratech Corp., Burlington, Mass., USA), using a 5- to 12-MHz multifrequency linear-array transducer. Once satisfactory images of near and far arterial walls were obtained, the transducer was secured and stabilized in a stereotactic clamp, and landmarks were made on the subject's skin to ensure similar placement of the transducer for subsequent FMD procedures and shear rate assessments within and between conditions. Subjects were encouraged to keep the landmarks between the 2 trials.

In addition to imaging the arterial dimensions, Doppler ultrasound was used to concurrently measure SFA blood velocity. Doppler flow signals were corrected at an insonation angle of 60°, and the sample volume was placed in the middle of the artery.

Diameter images and Doppler measurements of blood velocity were continuously recorded for 45 seconds at baseline prior to cuff inflation. The automatic blood pressure cuff was then rapidly inflated to 250 mmHg and maintained for 5 minutes until cuff deflation. Diameter and blood velocity recordings resumed prior to cuff deflation and continued for 5 minutes after deflation. Ultrasound images were continuously recorded at 5 frames•$s^{-1}$ with Camtasia (TechSmith, Okemos, Mich., USA), and stored as .avi files. This procedure was repeated hourly across the sitting intervals.

Arterial Diameters and Blood Velocities:

Off-line analysis of diameters was performed using automated edge-detection software (Brachial Analyzer, Medical Imaging Applications LLC, Coralville, IA, USA). This software allows the technician to determine a region of interest where the near and far vessel walls are most clear. The vessel wall borders are then detected using an optimal graph search-based segmentation that uses a combination of pixel density and image gradient as an objective function. All analyzed images were reviewed by the technician and edited when needed to ensure that diameter measurements were always determined from the intima-lumen interface at the near and far vessel wall. Blood velocities were determined using the systems and methods described herein after automated selection of the blood flow envelop throughout the measurement. The velocity-time integral was used to calculate the mean blood velocity for each cardiac cycle. Diameters and blood velocities were not ECG-gated. The peak dilation after cuff deflation was determined using the highest 3-s moving average and was presented as a percentage change from baseline diameter (FMD %). SFA shear rate was used as an estimate of arterial shear stress and was calculated for each FMD % at baseline and during the post occlusion period using the following formula:

$$4 \cdot Vm \cdot D{-1}$$

where Vm is mean blood velocity (cm• s−1) and D is mean arterial diameter (cm). All measurements and analysis were performed by a single researcher (ST) who was blinded to the participant identity and treatment condition for each image file.

Statistical analysis:

Descriptive analysis was performed to summarize subject characteristics (Table 1).

TABLE 1

| Variable | Value |
|---|---|
| N | 11 |
| Age (years) | 24.2 ± 4.4 |
| BMI (kg · m$^2$) | 23.6 ± 3.4 |
| Systolic blood pressure (mm Hg) | 116 ± 9.8 |
| Diastolic blood pressure (mm Hg) | 77.3 ± 6.5 |
| Total cholesterol (mg/dl) | 171.5 ± 32.7 |
| LDL cholesterol (mg/dl) | 98 ± 29.6 |
| HDL cholesterol (mg/dl) | 57.8 ± 13.6 |
| VLDL cholesterol (mg/dl) | 15.7 ± 9.8 |
| Triglycerides (mg/dl) | 78 ± 49 |
| Glucose (mg/dl) | 91 ± 6.5 |

Note:
Data represented mean ± SD

Within both trials, one way ANOVA was conducted on the baseline diameter as the dependent variable. Within the SIT trial, a one way ANOVA was conducted on the dependent variables baseline diameter, FMD %, antegrade shear rate, and mean shear rate, 8 isoprostane and total antioxidant capacity (TAC). When an effect was found, pairwise comparisons were used to locate significant differences across time from baseline. Observed effect size was reported for ANOVA interactions and main effects as partial eta squared ($\eta^2$). Comparisons across the two treatment conditions for FMD were performed using 2-way repeated measures ANOVA, evaluating whether the effect of sitting differed between conditions (with and without Vitamin C); again, pairwise comparisons were used to identify significant differences at each time point if the main effects were positive. All values are expressed as the mean ±standard error of the mean and the alpha level for statistical significance was set a priori at 0.05. All statistical calculations were performed using IBM SPSS Statistics 21.0 software (IBM SPSS Inc.).

Results:

Data for one time point FMD on one subject was not collected, and thus, this subject was omitted from all analysis. Data on eleven subjects are presented.

Oxidative Stress Biomarkers:

Blood was collected six times within a period of three hours for both the trials. Six subjects had complete data for each time point in the SIT trial. Data is presented for these six subjects.

Figure 6:
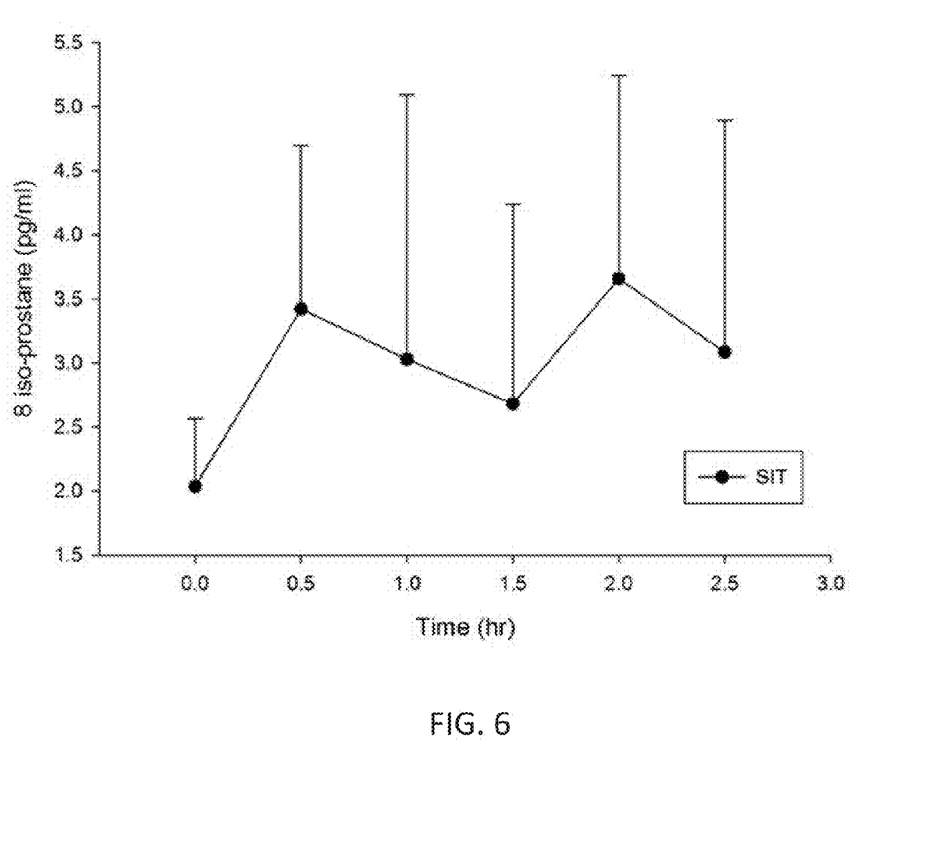
FIG. 6 is a graph showing plasma 8 iso-prostane measurements at baseline, 30 minutes, 1 hour, 1 hour 30 minutes, 2 hours and 3 hours during the SIT trial as measured in Example 1.

8 iso-prostane, which was recently reported as being one of the most sensitive markers of generalized oxidative stress, was measured (FIG. 6). There was no significant difference in 8 iso-prostane from baseline during 3 hours of sitting ($\eta^2$=0.149, P=0.511). It is hypothesized that this finding is a result of the blood being sampled from the arm, whereas the primary stimulus (low shear rate) from sitting was localized to the lower extremities. In this scenario, it may be plausible that the oxidative stress was below the level of detection in central circulation. During sitting, the physiological milieu between arms and legs are different with the leg vasculature being more prone to thrombosis. For example, 2 hours of sitting increased the viscosity in the leg, but not in the arms. For this specific reason, blood samples from the foot to access the local lower extremity circulation was attempted, but unsuccessful. Alternative explanations for non-significant changes in 8 iso-prostane may be that this particular assay may not be sensitive enough to pick up the limited increases in oxidative stress from prolonged sitting. Additionally, perhaps a longer bout of sitting may lead to a generalized expression of oxidative stress that may be able to be measured in the arm.

Figure 7:
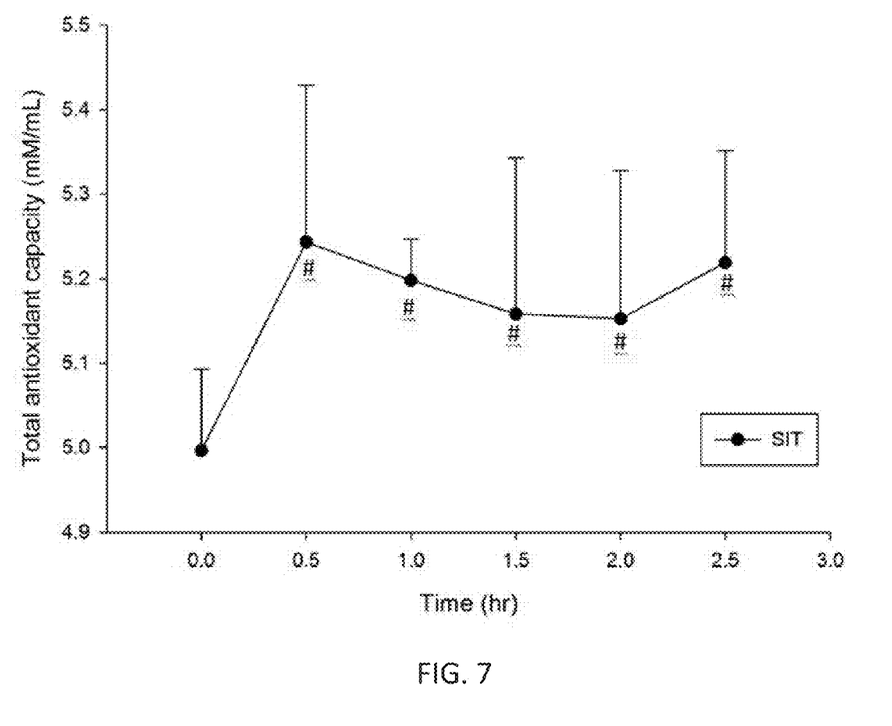
FIG. 7 is a graph showing plasma total antioxidant capacity measurements at baseline, 30 minutes, 1 hour, 1 hour 30 minutes, 2 hours and 3 hours during the SIT as measured in Example 1.

Total antioxidant capacity (TAC) was measured to evaluate if, during prolonged sitting there was a change in antioxidant defense, which is associated with increased oxidative stress. Repeated measures ANOVA yielded a significant difference in TAC across time in the SIT trial. Pairwise comparison from baseline uncovered a significant difference between baseline and 30 minutes, 1 hour, 1 hour 30 minutes, 2 hours, and baseline and 2 hours 30 minutes (p=0.002). Particularly, as shown in FIG. 7, in which # indicates significant difference from baseline (p≤0.05), TAC significantly increased at 30 minutes of the SIT trial as compared to baseline and stayed significantly higher during the 3 hours of sitting. It is hard to interpret this result; and it is against expectations.

TABLE 2

Shear rates (s−1) in the SFA during the SIT and VIT trials at baseline, 1 hour, 2 hours, and 3 hours.

| | SIT | | | | VIT | | | |
|---|---|---|---|---|---|---|---|---|
| | Baseline (0 hr) | 1 hr | 2 hr | 3 hr | Baseline (0 hr) | 1 hr | 2 hr | 3 hr |
| Antegrade | 7.7 ± 1.36 | 5.77 ± 2.39^ | 5.87 ± 2.17^ | 6.48 ± 1.79 | 7.03 ± 3.5 | 8.58 ± 6.91 | 6.56 ± 3.08 | 6.22 ± 2.39 |
| Mean | 5.03 ± 1.58 | 2.9 ± 2.94^ | 3.14 ± 1.23^ | 3.69 ± 1.28 | 5.17 ± 7.54 | 4.44 ± 4.23 | 2.99 ± 2.6 | 3.17 ± 2.14 |

SFA shear rates (s$^{-1}$) during SIT and VIT trials.
Data represented as Mean ± SD
^represent significantly different from 0 hr in SIT.

A chronic decrease in antegrade shear has been found to create a pro-atherogenic milieu and low mean shear rate has been implicated in reduced nitric oxide (NO) bioavailability and decreased activity of endothelial NO synthase. This theory was supported by the results in that there was a shear rate mediated decline in SFA endothelial function during 3 hours of prolonged sitting.

Baseline antegrade shear rate significantly declined from baseline to 3 hours of sitting (p=0.040). Pairwise comparisons located the significant decline between baseline and 1 hour (p=0.024) and baseline and 2 hours (p=0.024). No significant differences were found between baseline and 3 hours (p=0.130). Moreover, there was a significant decline in mean shear rates during the SIT trial (p=0.037). Pairwise comparisons revealed a significant difference between baseline and 1 hour (p=0.048), baseline and 2 hours (p=0.001), but not between baseline and 3 hours (p=0.064).

Figure 8:
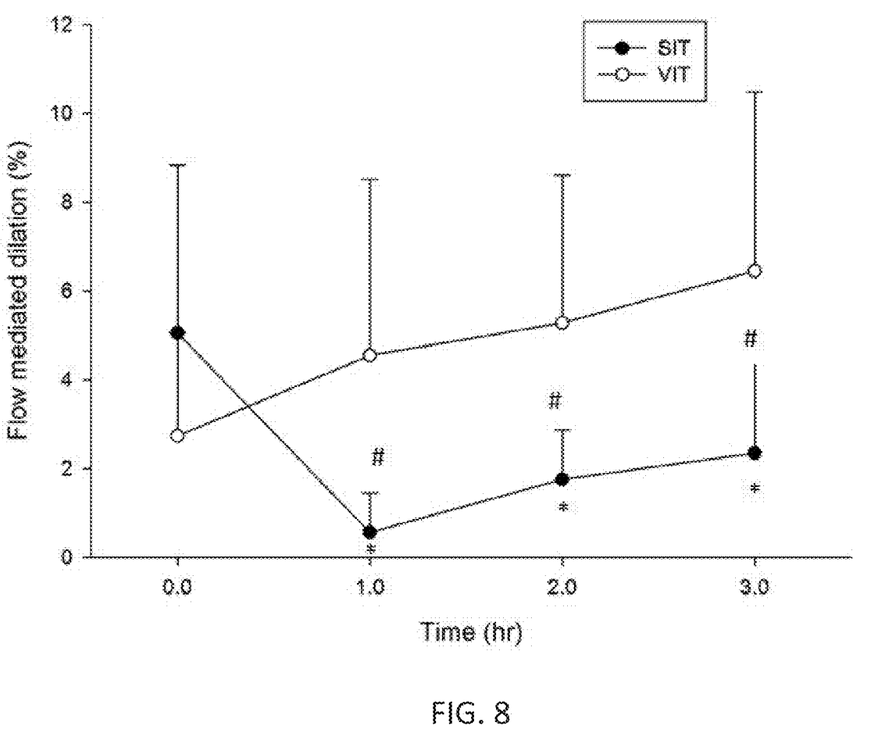
FIG. 8 is a graph showing flow mediated dilation in the superficial femoral artery during the sitting (SIT) and Vitamin C (VIT) trial as measured in Example 1.

FIG. 8 is a graph showing flow mediated dilation in the superficial femoral artery during the sitting (SIT) and Vitamin C (VIT) trial as measured in this Example. Error bars represent standard deviations. * indicates significant difference between trials at p≤0.05. # indicates significant difference from baseline. SFA FMD % between SIT and VIT (FIG. 8): There was a significant trial x time interaction for SFA FMD (P=0.037). The variable of interest was FMD % between each time point. There was a significant decline in FMD % from baseline during 3 hours of sitting (p=0.018). Pairwise comparisons indicated the difference to be between baseline and 1 hour (p=0.003), 2 hours (p=0.014) and 3 hours (p=0.013).

Pairwise comparisons were further conducted to investigate the differences between SIT and VIT FMD % at each hour. Baseline SFA FMD % did not differ between the two trials (p=0.093). However, FMD % was significantly different between trials at 1 hour (p=0.009), 2 hours (p=0.016) and 3 hours (p=0.004) with VIT preventing the decline of FMD.

These results indicate that endothelial function in the SFA is significantly impaired from baseline during a 3 hour bout of uninterrupted sitting, beginning sometime before the first hour. This suggests that this attenuation was an oxidative stress mechanism, based on the VIT trial.

Vitamin C and Endothelial Function:

It was further hypothesized that Vitamin C would prevent the decline in endothelial function during sitting. In the absence of blood biomarkers changing, Vitamin C provides suggestive evidence on the mechanisms for endothelial dysfunction during sitting. Vitamin C is an antioxidant and has been previously used in endothelial function to counteract oxidative stress from smoking, high fat meals, exercise and increased oscillatory shear.

The results (FIG. 8) showed that Vitamin C prevented the decline in SFA FMD during 3 hours of sitting suggesting a possible role of mechanisms involving oxidative stress playing a role in the decline of FMD during sitting. The dose of Vitamin C given to the subjects was higher than the recommended daily allowance and was expected to saturate their plasma. There are several potential pathways by which Vitamin C may have prevented the decline in SFA FMD during sitting.

Vitamin C has been known to restore NO activity and decrease the activation of vascular NADPH oxidase (a pro-oxidant). Vitamin C supplementation has previously been found to protect $BH_4$ and thus enzyme activity of eNOS. Vitamin C allows the recycling of $BH_3$ radicals to stabilize $BH_4$ in the presence of ROS, thereby maintaining NO production. Indeed, Vitamin C may have directly counteracted oxidative stress by scavenging elevated superoxide radicals. Thus, Vitamin C, when ingested at 30 minutes and 1 hour 30 minutes, prevented the decline in endothelial function during 3 hours of sitting. This may suggest that mechanisms involving oxidative stress may be present during prolonged sitting and may be counteracted by Vitamin C.

Alternative mechanisms that may attenuate endothelial function during prolonged sitting may be increased viscosity. Viscosity has been shown to be higher in the legs after a bout of 2 hours of sitting, and in the presence of low mean shear rates. Viscosity has been positively associated with increased coagulation and inflammatory markers which in turn have been strongly associated with impaired endothelial function. It is possible that Vitamin C counteracted the viscosity and inflammation in this Example. Indeed, plasma Vitamin C has anti-inflammatory effects and is inversely associated with viscosity. Additionally, skeletal muscle inactivity results in an increase in intracellular calcium concentration which may result in increased NAD(P)H oxidase activity resulting in elevated superoxide production. Although this mechanism involves oxidative stress, the source of oxidative stress in this mechanism is from the muscle. In summary, the results show that prolonged sitting led to an impairment of SFA endothelial function, which was counteracted by oral Vitamin C; hence suggestive of an oxidative stress mechanism.

Example 2

In this Example, the effect of prolonged sitting and breaks in sitting on endothelial function was analyzed. Particularly, prolonged sitting of subjects was studied to analyze its effects of superficial femoral artery (SFA) endothelial function. Further, the effect of breaking sitting time on SFA was also analyzed.

Similar to Example 1, this Example consisted of two screening visits and two sitting trials in random sequence, one with uninterrupted sitting (SIT) and one with breaks in sitting time (ACT). FMD measurements were conducted at baseline, 1 hour, 2 hours and 3 hours in both the trials.

Subjects and testing methods were used as described in Example 1 with the exception that the different sitting conditions of Example 2 included uninterrupted sitting (SIT) or breaks in sitting time (ACT) as opposed to sitting with or without Vitamin C as analyzed in Example 1. Particularly, for the ACT group, the subjects sat similar to the SIT trial, but walked on a treadmill for five minutes at 2 miles/hour at 30 minute, 1 hour 30 minute, and 2 hours 30 minute time points in each trial.

Twelve subjects, who comprised a homogenous group of apparently healthy inactive young men (Table 3), were tested. One time point FMD on one subject in the ACT trial was not collected, and thus, this subject's data was excluded from the two way ANOVA between trials.

TABLE 3

Subject demographics

| Variable | Value |
|---|---|
| N | 11 |
| Age (years) | 23.36 ± 3.23 |
| BMI (kg · m$^2$) | 23.85 ± 3.37 |
| Systolic blood pressure (mm Hg) | 116.45 ± 9.59 |
| Diastolic blood pressure (mm Hg) | 78 ± 6.05 |
| Total cholesterol (mg/dl) | 170.55 ± 32.66 |
| LDL cholesterol (mg/dl) | 98.27 ± 29.56 |
| HDL cholesterol (mg/dl) | 56.09 ± 13.20 |
| VLDL cholesterol (mg/dl) | 16.18 ± 9.62 |
| Triglycerides (mg/dl) | 80.36 ± 48.25 |
| Glucose (mg/dl) | 91.55 ± 6.07 |

Data are presented as mean ± SD

Results:

SIT trial: Superficial femoral artery baseline diameters are presented in Table 4. There was no significant difference between the baseline diameters from baseline to 3 hours ($\eta^2=0.112$, p=0.263).

TABLE 4

Baseline femoral artery diameters during SIT and ACT across the 3-hour periods

| | Baseline diameters (mm) | | | |
|---|---|---|---|---|
| | 0 hr | 1 hr | 2 hr | 3 hr |
| SIT | 6.32 ± 0.63 | 6.37 ± 0.71 | 6.52 ± 0.68 | 6.32 ± 0.74 |
| ACT | 6.50 ± 0.21 | 6.40 ± 0.17 | 6.31 ± 0.19 | 6.22 ± 0.21 |

Data presented as means ± SE

SFA FMD (FIG. 9): There was a significant reduction in FMD across time in SIT each hour, from baseline to 3 hours ($\eta^2=0.481$, p≤0.001). The FMD was significantly reduced at 1 hour, 2 hours and 3 hours as compared to baseline.

Figure 9:
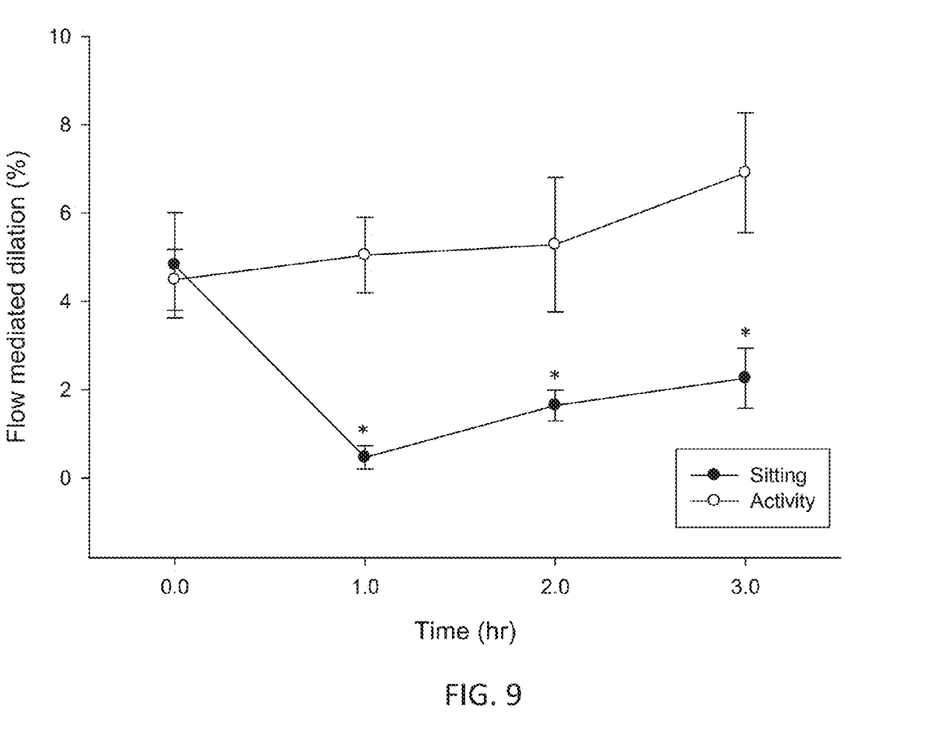
FIG. 9 is a graph showing flow mediated dilation in the superficial femoral artery during 3 hours of sitting during the sitting (SIT) and breaking sitting time (ACT trial) as measured in Example 2. Error bars represent standard error. # indicates significant difference from baseline in the SIT trial, * indicates significant difference between trials at $p \leq 0.05$.

SIT and ACT trial: A 2×4 (trial×time) repeated measures ANOVA was performed for the dependent variable FMD in the SIT and ACT trials. There was a significant trial×time interaction (p<0.05) between FMD and time across trials. The variable of interest was the FMD difference between trials at each measurement (baseline, 1 hour, 2 hours and 3 hours). FMD between the two trials was not significantly different at baseline. However, FMD was significantly reduced in the SIT trial, as compared to the ACT trial at 1 hour, 2 hours and 3 hours (FIG. 9).

It was hypothesized that 3 hours of sitting would lead to a shear mediated decline in superficial femoral artery (SFA) endothelial function as measured by flow mediated dilation (FMD) and as further shown in Example 1. Secondly, it was hypothesized that systematic low intensity physical activity (5 minutes at 2 miles hr$^-$) would prevent the decline in FMD. Indeed, the results show a significant attenuation of SFA FMD on 3 hours of sitting that was associated with reductions in shear rates. It was also observed that when breaks with modest activity were added during the sitting time, the decline in FMD was not observed.

Baseline antegrade shear rate: A significant decline in the antegrade shear rate from baseline to 3 hours ($\eta^2=0.209$, p=0.049) was found. The antegrade shear rate was significantly lower at 1 hour and 2 hours as compared to baseline.

Mean shear rate: There was a significant decline in mean shear rate from baseline across time ($\eta^2=0.237$, p=0.028). Mean shear rate was significantly lower at 1 hour and 2 hours as compared to baseline. Shear rate data are presented in Table 5.

TABLE 5

Shear rates (s$^{-1}$) in the SFA during the SIT and ACT trial at baseline, 1 hr, 2 hr and 3 hr

| | SIT | | | | ACT | | | |
|---|---|---|---|---|---|---|---|---|
| | 0 hr | 1 hr | 2 hr | 3 hr | 0 hr | 1 hr | 2 hr | 3 hr |
| Antegrade | 7.14 ± 0.69 | 5.26 ± 0.79 | 5.66 ± 0.72 | 5.89 ± 0.55 | 5.87 ± 0.83 | 8.34 ± 2.92 | 5.45 ± 0.71 | 5.61 ± 0.85 |
| Retrograde | 2.62 ± 0.36 | 2.83 ± 0.54 | 2.85 ± 0.45 | 2.51 ± 0.32 | 2.23 ± 0.40 | 3.02 ± 0.55 | 2.51 ± 0.44 | 2.92 ± 0.43 |
| Mean | 4.53 ± 0.66 | 2.42 ± 0.96 | 2.81 ± 0.50 | 3.38 ± 0.47 | 3.64 ± 0.62 | 5.32 ± 2.90 | 2.94 ± 0.69 | 2.69 ± 0.60 |
| Peak | 52.04 ± 21.20 | 19.22 ± 4.27 | 27.38 ± 4.41 | 23.01 ± 3.10 | 22.14 ± 8.67 | 21.44 ± 2.31 | 18.85 ± 2.86 | 19.01 ± 2.04 |
| SRauc* | 838.7 ± 134.3 | 442.6 ± 178.7 | 363.8 ± 127.3 | 580.2 ± 136.4 | 296.4 ± 132.7 | 321.8 ± 134.6 | 299.5 ± 127.2 | 477.4 ± 106.7 |

SFA shear rates (s–1) during SIT and ACT trials.
Data represented as Mean ± SE
*SRauc data is represented for 4 subjects. The number of data points with FMD % = 0 in SIT trial were 1, 6, 1, 2 at baseline, 1 hr, 2 hr, and 3 hr, respectively Particularly, mean shear rates during the 3 hours of sitting significantly declined from baseline by hour 1, and stayed low all through the 3 hours of sitting. These results suggest that sitting creates a milieu of low mean shear rate and corresponds to the decline in FMD.

Another interesting finding from this Example is the progressive decline in antegrade shear. Antegrade shear represents forward flow through the (superficial femoral) artery. Even in the absence of overt atherosclerosis, a chronic decrease in antegrade shear creates a pro-atherogenic milieu. Hence, it is hypothesized that repeated bouts of prolonged sitting may contribute to vascular aging, at least in the lower extremities.

In summary, a significant difference in FMD between the SIT and ACT trials at 1 hour, 2 hours, and 3 hours was observed; with no significant difference observed at baseline. No significant difference, however, was observed in the mean shear rate between these trials. The ACT subjects performed light intensity physical activity at 30 minutes, 1 hour 30 minutes and 2 hour 30 minutes during the sitting interval. Even this very light intensity physical activity prevented the decline in FMD that was seen in the SIT trial, and may explain the protective effect against sitting-induced impairment in FMD. Mean shear rate observations between trials are not different perhaps because of the timing of measurement. There was a lag of ~25 minutes between the activity and the shear rate measurement. It is possible that the flow ephemerally increased on walking and had decreased close to baseline at the time of measurement.

There are at least three mechanisms that may explain the attenuation in FMD during sitting and its mitigation after breaking sitting time. These mechanisms may act separately or may be integrated. First, in the seated position, the shear rates are lower than in supine position. Once sitting commences, these shear rates initially decline and are maintained creating a condition of low flow in the lower extremity (as seen in the Examples' measurements). Conditions of low flow have been associated with impaired endothelial function. In the above Examples, a decline in SFA FMD during 3 hours of sitting was observed, which was associated with concurrent reductions in shear forces. Although no prior evidence exists which directly demonstrates the effects of exercise on shear in the SFA, it is logical that the low intensity activity in the Examples episodically increased shear rate in the SFA (and other leg vessels). The brief intervals of low-level activity in the ACT trial group appeared to have been sufficient to prevent sitting-related reductions in shear.

A second mechanism can be blood viscosity. Viscosity has been shown to be higher in the legs after 2 hours of sitting. Increased viscosity has been associated with increased coagulation and inflammatory markers, which in turn have been strongly associated with impaired endothelial function. Low shear rates are associated with clumping of red blood cells and increased viscosity. Conversely, increased shear rates from walking (ACT) would intermittently oppose the rise in viscosity and coagulation markers, resulting in preserved FMD.

A third mechanism is an increased muscle sympathetic nerve activity (MSNA). MSNA is higher during the upright sitting posture and along with increased blood pressure may result in a decline in FMD. Indeed, increased MSNA is also linked to increased pro-atherogenic shear patterns in the conduit arteries. Walking induced muscular contractions would help in venous return thereby not requiring the sympathetic outflow compensation during prolonged sitting. In addition, light intensity activity has been known to directly decrease MSNA. In Example 2, the light intensity walking may have ephemerally lowered the MSNA and preserved shear patterns and FMD.

This written description uses examples, including the best mode, to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for simultaneously analyzing antegrade and retrograde blood flow, said method implemented using an ultrasound computing device including a processor in communication with a memory, said method comprising:
   receiving, by the computing device, a first plot of blood velocities over time;
   determining, by the computing device, a first amount of blood flow based on the first plot, the first amount is associated with antegrade blood flow;
   determining, by the computing device, a second amount of blood flow based on the first plot, the second amount is associated with retrograde blood flow;
   wherein the determining, by the computing device, the first amount of blood flow based on the first plot is simultaneous with the determining, by the computing device, the second amount of blood flow based on the first plot;
   determining, by the computing device, a mean amount of blood flow based at least in part on the first amount of blood flow and the second amount of blood flow; and
   storing at least one of the first amount of blood flow, the second amount of blood flow, and the mean amount of blood flow in the memory.

2. The method of claim 1, wherein receiving the first plot further comprises receiving, by the computing device, a plurality of plots, including the first plot, each plot corresponding to a fixed time period.

3. The method of claim 2, further comprising determining the first amount of blood flow, the second amount of blood flow, and the mean amount of blood flow for each fixed time period.

4. The method of claim 1, further comprising:
   identifying a portion of the first plot that corresponds to a most recent output of the ultrasound computing device over the fixed time period; and
   determining the first amount of blood flow, the second amount of blood flow, and the mean amount of blood flow based on the identified portion.

5. The method of claim 1, further comprising:
   receiving, by the ultrasound computing device, a first image generated by an ultrasound computing device; and
   identifying the first plot in the first image.

6. The method of claim 5, further comprising:
   receiving an input designating at least one reference point on the first image; and
   identifying the first plot based at least in part on the at least one reference point.

7. The method of claim 1, further comprising:
   receiving, by the ultrasound computing device, a video comprising a plurality of images generated by the ultrasound computing device;
   identifying the first plot in a first image of the plurality of images; and
   identifying at least a second plot in a second image of the plurality of images.

8. The method of claim 7, further comprising:
   determining a number of frames per second from the plurality of images; and
   determining a fixed time period associated with each plot based on the frames per second.

9. The method of claim 1, further comprising identifying, by the computing device, a maximum blood velocity, based at least in part on the first plot.

10. The method of claim 1, further comprising determining, by the ultrasound computing device, an average blood velocity based at least in part on the first plot.

11. An ultrasound computing device for simultaneously analyzing antegrade and retrograde blood flow, said ultrasound computing device comprising a processor in communication with a memory device, said ultrasound computing device configured to:
receive a first plot of blood velocities over time;
determine a first amount of blood flow based on the first plot, the first amount is associated with antegrade blood flow;
determine a second amount of blood flow based on the first plot, the second amount is associated with retrograde blood flow;
wherein the determining the first amount of blood flow based on the first plot is simultaneous with the determining the second amount of blood flow based on the first plot;
determine a mean amount of blood flow based at least in part on the first amount of blood flow and the second amount of blood flow; and
store at least one of the first amount of blood flow, the second amount of blood flow, and the mean amount of blood flow in the memory device.

12. The computing device of claim 11, further configured such that receiving the first plot further comprises receiving a plurality of plots, including the first plot, each plot corresponding to a fixed time period.

13. The ultrasound computing device of claim 12, further configured to determine the first amount of blood flow, the second amount of blood flow, and the mean amount of blood flow for each fixed time period.

14. The ultrasound computing device of claim 11, further configured to:
identify a portion of the first plot that corresponds to a most recent output of the ultrasound computing device over the fixed time period; and
determine the first amount of blood flow, the second amount of blood flow, and the mean amount of blood flow based on the identified portion.

15. The ultrasound computing device of claim 11, further configured to:
receive a first image generated by the ultrasound computing device; and
identify the first plot in the first image.

16. The computing device of claim 15, further configured to:
receive an input designating at least one reference point on the first image; and
identify the first plot based at least in part on the at least one reference point.

17. The ultrasound computing device of claim 11, further configured to:
receive a video comprising a plurality of images generated by an ultrasound computing device;
identify the first plot in a first image of the plurality of images; and
identify at least a second plot in a second image of the plurality of images.

18. The ultrasound computing device of claim 17, further configured to:
determine a number of frames per second from the plurality of images; and
determine a fixed time period associated with each plot based on the frames per second.

19. A computer-readable storage medium having computer-executable instructions embodied thereon, wherein when executed by an ultrasound computing device having a processor in communication with a memory device, the computer-executable instructions cause the computing device to:
receive a first plot of blood velocities over time;
determine a first amount of blood flow based on the first plot, the first amount is associated with antegrade blood flow;
determine a second amount of blood flow based on the first plot, the second amount is associated with retrograde blood flow;
wherein the determining the first amount of blood flow based on the first plot is simultaneous with the determining the second amount of blood flow based on the first plot;
determine a mean amount of blood flow based at least in part on the first amount of blood flow and the second amount of blood flow; and
store at least one of the first amount of blood flow, the second amount of blood flow, and the mean amount of blood flow in the memory device.

20. The computer-readable storage medium of claim 19, further comprising computer-executable instructions such that receiving the first plot further includes receiving, by the computing device, a plurality of plots, including the first plot, each plot corresponding to a fixed time period.

* * * * *